United States Patent [19]

Nojima et al.

[11] Patent Number: 4,562,005
[45] Date of Patent: Dec. 31, 1985

[54] 2-METHOXYPROPYL PHOSPHATE DERIVATIVES

[75] Inventors: Shoshichi Nojima, Tokyo; Hiroaki Nomura, Osaka, both of Japan

[73] Assignee: Takeda Chemical Industries, Ltd., Osaka, Japan

[21] Appl. No.: 585,415

[22] Filed: Mar. 2, 1984

[30] Foreign Application Priority Data

Apr. 4, 1983 [JP] Japan .................. 58-59833

[51] Int. Cl.$^4$ .............................. A23J 7/00
[52] U.S. Cl. ................... 260/403; 260/925; 260/945
[58] Field of Search ............. 260/945, 403, 925

[56] References Cited

U.S. PATENT DOCUMENTS

| | | | |
|---|---|---|---|
| 4,159,988 | 7/1979 | Eible et al. | 260/925 |
| 4,408,052 | 10/1983 | Hozumi et al. | 546/22 |
| 4,426,525 | 1/1984 | Hozumi et al. | 260/945 |
| 4,504,474 | 3/1985 | Hanahan et al. | 260/403 |

FOREIGN PATENT DOCUMENTS

| | | |
|---|---|---|
| 0050460 | 10/1981 | European Pat. Off. . |
| 0061872 | 3/1982 | European Pat. Off. . |
| 0071892 | 7/1982 | European Pat. Off. . |
| 2642661 | 3/1978 | Fed. Rep. of Germany . |
| 3239858 | 1/1984 | Fed. Rep. of Germany . |
| 772649 | 5/1977 | South Africa . |
| 772648 | 5/1977 | South Africa . |

OTHER PUBLICATIONS

Takeda Yakuhin Kogy (1 page).
Toyama Chem KK (1 page).
Cancer Research, vol. 38, Effect of Lysolecithin and Analogs on Mouse Ascites Tumors, Tarnowski, Mountain, Stock, Munder, Weltzien and Westphal.
Cancer Research, vol. 39, Disturbance of Phospholipid Metabolism During the Selective Destruction of Tumor Cells Induced by Alkyl-Lysophospholipids, Modolell.

*Primary Examiner*—Anton H. Sutto
*Assistant Examiner*—Elizabeth A. Flaherty
*Attorney, Agent, or Firm*—Wegner & Bretschneider

[57] ABSTRACT

Novel phospholipids, inclusive of pharmaceutically acceptable salts thereof, of the formula

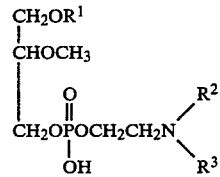

wherein $R^1$ is an aliphatic hydrocarbon residue of 15 to 20 carbon atoms, $R^2$ is an alkyl group of 1 to 4 carbon atoms and $R^3$ is a hydrogen atom or an alkyl group of 1 to 4 carbon atoms, exhibit inhibitory activity to multiplication of tumor cells and are useful for inhibiting multiplication of tumor cells and prolonging the survival time of tumor-bearing warm-blooded animal.

10 Claims, No Drawings

2-METHOXYPROPYL PHOSPHATE DERIVATIVES

This invention relates to novel phospholipids. More particularly, this invention relates to a compound of the formula

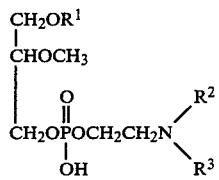
(I)

wherein $R^1$ is an aliphatic hydrocarbon residue of 15 to 20 carbon atoms, $R^2$ is a lower alkyl group; $R^3$ is a hydrogen atom or a lower alkyl group, or an acid or base addition salt thereof.

Phospholipids are broadly distributed in living bodies where they exist particularly as components of the membranes and are involved in a variety of important biological phenomena through modulation of membrane functions. The present inventors synthesized compounds of the above formula (I) which have not been found in nature, and found that these compounds have excellent antitumor activity.

Referring to the above formula (I), the aliphatic hydrocarbon residue of 15 to 20 carbon atoms as represented by $R^1$ may for example be a straight-chain or branched group, saturated or unsaturated. Thus, for example, $C_{15-20}$ alkyl groups (e.g. n-pentadecyl, n-hexadecyl, n-heptadecyl, n-octadecyl, n-nonadecyl, n-eicosanyl, 4-methylpentadecyl, 6,10-dimethylpentadecyl, 6,10,14-trimethylpentadecyl, 3,7,11-trimethyldodecyl, 7,11,15-trimethylhexadecyl, 6,10,14-trimethylheptadecyl, 3,7,11,15-tetramethylhexadexyl), $C_{15-20}$ alkenyl groups (e.g. 3-pentadecenyl, 4-hexadecenyl, 3-heptadecenyl, 9-octadecenyl, 9-nonadecenyl, 9,12-octadecadienyl, 7,11,15-trimethyl-5-hexadecenyl, 3,7,11-trimethyl-2,6,10-dodecatrienyl, 3,7,11,15-tetramethyl-2,6,10,14-hexadecatetraenyl), and $C_{15-20}$ alkynyl groups (e.g. 3-pentadecanynyl, 4-hexadecanynyl, 3-heptadecanynyl, 9-octadecanynyl, 3-nonadecanynyl, 4-eicosanynyl) may be mentioned. When $R^1$ is an alkenyl group, both the E- and Z-configurations are included. These groups may have such substituent groups as hydroxy, mercapto, carbamoyl, phenyl, halogen, carboxy, oxo, etc.

Referring to the formula (I), the lower alkyl group represented by $R^2$ or $R^3$ may be a straight-chain or branched alkyl group of about 1 to 4 carbon atoms, such as methyl, ethyl, propyl, isopropyl, butyl, isobutyl, sec-butyl, tert-butyl, etc.

The salt of the compound (I) includes pharmaceutically acceptable salt such as salts with inorganic acids, e.g. hydrochloride, hydrobromide, sulfate, nitrate, phosphate, etc.; fumarate, maleate, toluenesulfonate, methanesulfonate, etc.; metal salts such as salts with sodium, potassium, calcium, magnesium, aluminum, etc.; and salts with bases such as ammonium, hydrazine, guanidine, triethylamine, dicyclohexylamine, quinine, cinchonine salts, etc. The salt of compound (I) can be obtained by, for example, addition of a corresponding acid, alkali or base. Depending on its kind, the acid addition salt may exist in the form of

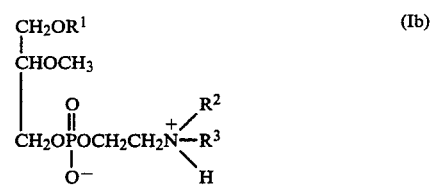
(Ia)

wherein $R^1$, $R^2$ and $R^3$ are as defined hereinbefore and X- is an anion such as chloride or bromide. Moreover, the compound (I) may exist in the form of

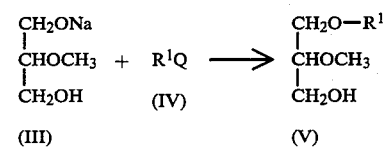
(Ib)

wherein all symbols are as defined hereinbefore.

The compound (I) according to this invention contains at least one asymmetric carbon atom within its molecule and, therefore, may be R- configured or S- configured. Each of these stereoisomers and a mixture thereof also fall within the scope of the invention.

The compound (I) can be produced for example by the following processes.

PROCESS A

The sodium salt of 2-O-methylgylcerol (II) [synthesized in accordance with the process described in Journal of Chemical Society 1934, 1234 or Ann. 709, 2421 (1967)] is dissolved or suspended in an inert solvent under anhydrous conditions. Then, a compound of the formula $R^1Q$ wherein $R^1$ is as defined hereinbefore and Q is a halogen or a sulfate or sulfonate radical, is permitted to act on said salt to give a compound of the formula (V) wherein $R^1$ is as defined hereinbefore.

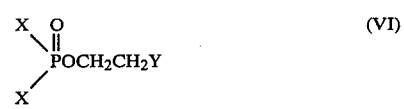

The compound (V) is reacted with a compound of the formula $$\begin{array}{c} X \\ \diagdown \\ \phantom{X}\diagup \\ X \end{array} \!\!\! \begin{array}{c} O \\ \| \\ P \end{array} OCH_2CH_2Y \qquad (VI)$$

wherein X and Y each is a halogen atom (e.g. chlorine, bromine, iodine) and, then, water is permitted to act on the reaction product to give a compound of the formula

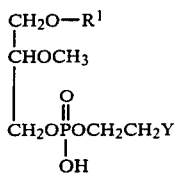

(VII)

wherein $R^1$ and Y are as defined hereinbefore. The compound (VII) is then reacted with a compound of the formula

(VIII)

wherein all symbols are as defined hereinbefore, to give the desired compound (I) or a salt thereof such as the salt (Ia).

PROCESS B

The compound (V) is reacted with a compound of formula

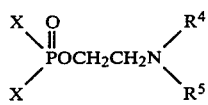

(VI')

wherein X is as defined hereinbefore and $R^4$ and $R^5$ are such that either one is $R^2$ which is defined as hereinbefore, with the other being benzyl, benzyloxycarbonyl, phenoxycarbonyl, formyl, trifluoroacetyl, benzylcarbonyl, trimethylsilyl or triphenylmethyl. The reaction product is then treated with water, followed by a deprotection reaction performed in the known manner to give a compound of formula

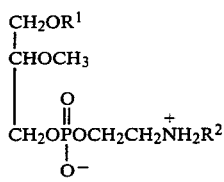

(I')

wherein $R^1$ and $R^2$ are as defined hereinbefore, which is among the compound (I).

PROCESS C

The commpound (VII) is reacted with a compound of the formula

(VIII')

wherein $R^4$ and $R^5$ are as defined hereinbefore, followed by a deprotection reaction performed in the known manner to give the compound (I').

The present inventors discovered that the compound of the formula (I) has an excellent antitumor activity and that it is less liable to cause adverse reactions than the known compound of the formula

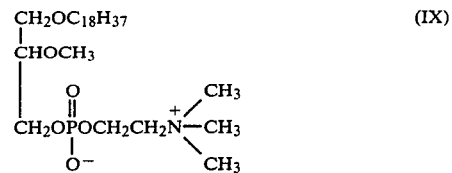

(IX)

Thus, the compound (I) according to this invention in a dose of 0.25 to 2 mg/mouse/day produces significant tumor growth inhibiting and life span prolonging effects in tumor-bearing mice such as mice Sarcoma 180, Meth A Sarcoma, mouse mammary cancer MM46, etc. (Table 1). The compound (I) also exhibits a potent growth inhibiting effect on mouse myeloid leukemia cell M1 and human promyelocytic leukemia cells HL-60.

The outstanding advantage of the compound (I) over the compound of formula (IX) is that the former is less liable to cause adverse effects. Thus, whereas the compound (IX) is known to have platelet aggregating activity [Biochemical and Biophysical Research Communications 99, 183 (1981)], the compound (I) according to this invention has been found to be completely free from such activity. Furthermore, whereas compound (IX) has a depressor effect on blood pressure as is evident from the test example given hereinafter, the compound of this invention has not be found to cause such effect. Platelet aggregating activity may induce various cardiovascular disorders while depressor or hypotensive action as such is a serious side effect, and when a compound having such activities is used as an antitumor drug, they produce toxic reactions. Notwithstanding the fact that it is free from such activities, the compound (I) according to this invention displays a life span prolonging action at least comparable to, or even surpassing, that of compound (IX) in animals bearing various tumors.

Therefore, the present compound (I) or a salt thereof can be used as a low-toxicity antitumor drug for tumor-bearing warm-blooded animals.

For use as an antitumor drug, the compound (I) can be made available in various pharmaceutical dosage forms such as injections, tablets, capsules, liquids, ointments, etc. and be safety administered either parenterally or orally.

Such injections inclusive of drip injections can be prepared in the routine manner using physiological saline or an aqueous solution containing glucose or/and other adjuvants. The tablets, capsules, etc. can also be prepared in the conventional manner. These compositions can be made available in unit dosage forms, and according to the purpose of administration, can be administered, taking injections as an example, intravenously, subcutaneously, directly to the lesion or otherwise.

The dosage for tumor-bearing warm-blooded animals is usually about 0.5 to 200 mg/kg (body weight), preferably about 2 to 50 mg/kg (body weight) as compound (I), the optimum dose level being selected from the above range according to the condition, route of administration, etc. As to administration schedules, the drug may be administered daily or at an interval of 2 to 7 days. In order to maintain an effective tissue concentration of the drug for a long time, the drug can be administered at the frequency of once to 3 times daily or by drip intravenous injection over a protracted time.

The following examples, preparation examples and test examples illustrate the present invention in more detail. However, they are by no means limitative of the present invention.

EXAMPLE 1

3-Octadecyloxy-2-methoxypropyl 2-dimethylaminoethyl phosphate

In 40 ml of benzene were dissolved 2.86 g (8 mmoles) of 3-octadecyloxy-2-methoxy-1-propanol and 2.52 g (10.4 mmoles) of 2-bromoethyl phosphorodichloridate, and a solution of 0.82 g (10.4 mmoles) of pyridine was added dropwise to the above solution. The mixture was stirred at room temperature for 5 hours. The solvent was evaporated off and 60 ml of water was added to the residue. The mixture was refluxed for 1.5 hours, cooled and extracted with ether. The extract was washed with water, dried over sodium sulfate and filtered. The filtrate was then concentrated. To the resultant colorless solid was added 48 ml of a 20% dimethylamine-toluene solution and the mixture was allowed to stand for 24 hours. The solvent was then evaporated off and 200 ml of methanol and 2.87 g (10.4 mmoles) of silver carbonate were added to the residue. The mixture was refluxed for one hour and filtered when hot. The filtrate was concentrated and the residue was chromatographed on a silica gel (60 g) column, elution being carried out with chloroform-methanol-water (65:25:4) to give the above-identified compound as a colorless crystalline powder. Yield 2.3 g (57%).

IR spectrum (KBr) cm$^{-1}$: 2920, 2850, 1460, 1220, 1060-1090.

NMR spectrum (60 MHz, CDCl$_3$) δ: 0.88(3H), 1.22(32H), 2.84(6H, s, —N(CH$_3$)$_2$), 3.1-3.4(2H, —CH$_2$N), 3.41(3H, OCH$_3$), 3.5-4.2(9H).

Elemental analysis: Calcd. for C$_{26}$H$_{56}$NO$_6$P.H$_2$O: C, 59.19; H, 11.08; N, 2.65; P, 5.87. Found: C, 59.29; H, 11.40; N, 2.66; P, 5.89.

EXAMPLE 2

(2S)-3-Octadecyloxy-2-methoxypropyl 2-dimethylaminoethyl phosphate

(i) 1,2-Isopropylidene-3-octadecyl-sn-glycerol

In a mixture of 200 ml of dimethyl sulfoxide and 120 ml of tetrahydrofuran were dissolved 10.6 g of 1,2-isopropylidene-D-glycerol and 31 g of octadecyl bromide, and 22.4 g of potassium hydroxide was added. The mixture was stirred vigorously. After 2.5 hours, the reaction mixture was poured into 500 ml of cold water and extracted with 700 ml of ethyl acetate. The extract was washed with water, dried and concentrated. The residue was purified by silica gel column chromatography [eluent: n-hexane-ethyl acetate (10:1)] to give 21.2 g of the above-identified compound.

[α]$_D$= +7.3° (c=1, CHCl$_3$)

(ii) 3-Octadecyl-sn-glycerol

In 30 ml of dioxane was dissolved 5.7 g of the above-obtained isopropylidene compound, and 3 ml of 10% hydrochloric acid was added. The mixture was stirred at room temperature overnight. The solvent was then evaporated off and the residue was recrystallized from methanol to give 4.4 g of the above-identified compound.

IR spectrum (KBr) cm$^{-1}$: 3410, 3330, 2915, 2850, 1455, 1120, 720.

NMR spectrum (60 MHz, CDCl$_3$) δ: 0.87(3H, t), 1.27(32H, m), 3.3-3.8(5H, m).

[α]$_D$= −1.9° (c=1, CHCl$_3$)

M.p. 70°-71° C.

(iii) 3-Octadecyl-1-trityl-sn-glycerol

In 30 ml of pyridine was dissolved 4.3 g of the above-obtained glycerol compound, and 3.48 g of trityl chloride was added. The mixture was stirred at room temperature overnight. The solvent was then evaporated off and the residue was purified by silica gel column chromatography (eluent: chloroform) to give 5.3 g of the above-identified compound.

IR spectrum (film) cm$^{-1}$: 3450, 3080, 3050, 2920, 2850, 1590.

NMR spectrum (60 MHz, CDCl$_3$) δ: 0.88(3H, t), 1.27(32H,m), 2.43(1H, d, OH), 3.2-3.6(6H, m), 3.95(1H, m), 7.36(15H, m).

[α]$_D$= −2.4° (c=1, CHCl$_3$)

M.p. 58° C.

(iv) 3-Octadecyl-2-methyl-sn-glycerol

In a mixture of 83 ml of dimethyl sulfoxide and 50 ml of tetrahydrofuran were dissolved 5.3 g of the above-obtained trityl compound and 6.4 g of methyl iodide, and 5.1 g of potassium hydroxide powder was added. The mixture was stirred for 2.5 hours and then treated in the conventional manner to give 5.0 g of 3-octadecyl-2-methyl-1-triyl-sn-glycerol. To this methylated compound was added 100 ml of 80% acetic acid and the mixture was stirred at 70° C. for 3 hours. The solvent was then evaporated off under reduced pressure and the residue was purified by chromatography on a silica gel column to give 2.3 g of the above-identified compound.

IR spectrum (film) cm$^{-1}$: 3400, 2925, 1470, 1120, 720.

NMR spectrum (60 MHz, CDCl$_3$) δ: 0.88(3H, t), 1.25(32H, m), 2.36(1H, t, OH), 3.46(3H, s), 3.2-3.9(7H, m).

[α]$_D$= +9.4° (c=1, CHCl$_3$)

(v) (2S)-3-Octadecyloxy-2-methoxypropyl 2-dimethylaminoethyl phosphate

In 10 ml of benzene was dissolved 230 mg of the above-obtained alcohol compound, and 313 mg of bromoethyl phosphorodichloridate was added, followed by addition of 0.12 of pyridine with ice-cooling. The mixture was stirred at room temperature for 3 hours and concentrated to dryness. To the residue were added 10 ml of water and 0.2 ml of hydrochloric acid acid and the mixture was refluxed for 40 minutes, cooled and extracted with ether. The extract was washed with water and concentrated and the residue was dissolved in 3 ml of toluene containing 0.6 g of dimethylamine. The solution was stirred overnight and concentrated to dryness. The residue was purified by chromatography on a silica gel column (eluent: methanol) to give 295 mg of the above-identified compound as a colorless solid.

IR spectrum (KBr) cm$^{-1}$: 3420, 2920, 2850, 1465, 1230, 1090.

NMR spectrum (60 MHz, CDCl$_3$) δ: 0.88(3H, t), 1.27(32H, m), 2.76(6H, s), 3.43(3H, s), 3.0-4.4(11H, m).

Elemental analysis: Calcd. for C$_{26}$H$_{56}$NO$_6$P.0.5H$_2$O: C, 60.20; H, 11.08; N, 2.70; P, 5.79. Found: C, 59.92; H, 10.88; N, 2.85; P, 5.79.

[α]$_D$= +1.0° (c=1, CHCl$_3$)

EXAMPLE 3

2-Methoxy-3-octadecyloxypropyl 2-methylaminoethyl phosphate

In 40 ml of benzene were dissolved 2.86 g (8 mmoles) of 3-octadecyloxy-2-methoxy-1-propanol and 2.52 g (10.4 mmoles) of 2-bromoethyl phosphorodichloridate, and a solution of 0.82 g (10.4 mmoles) of pyridine in benzene was added dropwise to the solution. The mixture was stirred at room temperature for 5 hours and the solvent was evaporated off. To the residue was added 60 ml of water and the mixture was refluxed for 1.5 hours, cooled and extracted with chloroform. The extract was washed with water, dried over sodium sulfate and filtered. The filtrate was then concentrated. To the resultant colorless solid were added 3.88 g (32 mmoles) of benzylmethylamine and then 20ml of toluene. The solution was allowed to stand for 4 days and concentrated. To the residue was added water and the mixture was acidified with hydrochloric acid and extracted with chloroform. The extract was dried over sodium sulfate and filtered. The filtrate was concentrated to give an oil, which was purified by silica gel (40 g) column chromatography, elution being carried out with chloroform-methanol-water (65:25:4) to give 3 g (64%) of a benzyl compound as a colorless powder. In 80 ml of acetic acid was dissolved 3 g of the above benzyl compound, and to the solution was added 1 g of 5% palladium-on-carbon. Catalytic reduction was carried out at atmospheric pressure. The reaction mixture was filtered and the filtrate was concentrated under reduced pressure. The residue was purified by silica gel (80 g) column chromatography. The colorless solid obtained from the methanol eluate was reprecipitated from chloroform-acetone to give the above-identified compound as a colorless crystalline powder. Yield 2 g.

IR spectrum (KBr) cm$^{-1}$: 2920, 2850, 1467, 1225, 1080, 960.

NMR spectrum (60 MHz, CDCl$_3$) δ: 0.87(3H), 1.24(32H), 2.63(3H, —NCH$_3$), 2.93–3.15(2H, —CH$_2$N), 3.28–3.55(8H), 3.75–4.25(4H), 7.64(2H, —NH+—OH).

Elemental analysis: Calcd. for C$_{25}$H$_{54}$NO$_6$P.H$_2$O: C, 58.45; H, 10.99; N, 2.73; P, 6.03. Found: C, 58.62; H, 11.19; N, 2.85; P, 6.31.

EXAMPLE 4

3-(3,7,11,15-Tetramethyl-2,6,10,14-hexadecatetraenyloxy)-2-methoxypropyl 2-dimethylaminoethyl phosphate (i) 3-(3,7,11,15-Tetramethyl-2,6,10,14-hexadecatetraenyloxy)-2-methoxypropanol In a mixture of 20 ml of dimethyl sulfoxide and 12 ml of tetrahydrofuran were dissolved 2.2 g of 3-(3,7, 11,15-tetramethyl-2,6,10,14-hexadecatetraenyl bromide and 2.3 g of 2-O-methylglycerin, and 2.0 g of powdered potassium hydroxide was added. The mixture was stirred for 2 hours, poured into cold water and extracted with ethyl acetate. The extract was washed with water, dried and concentrated. The residue was purified by chromatography on a silica gel column to give 1.15 g of the above-identified compound as light-yellow liquid.

IR spectrum (film) cm$^{-1}$: 3420, 2970, 2930, 2860, 1665, 1450, 1385, 1110, 1080.

NMR spectrum (90 MHz, CDCl$_3$) δ: 1.59(9H, s), 1.67(6H, s), 2.00, 2.04(12H, m), 3.44(3H, s), 3.33–3.80(3H, m), 4.01(2H, d), 5.10(3H, m), 5.33(1H, t).

(ii) 3-(3,7,11,15-Tetramethyl-2,6,10,14-hexadecatetraenyloxy)-2-methoxypropyl 2-dimethylaminoethyl phosphate In 20 ml of benzene was dissolved 1.15 g of the above alcohol compound, and 1.25 g of bromoethyl phosphorodichloridate and 0.41 g of pyridine were added dropwise. The mixture was stirred at room temperature for 3 hours and 4 ml of water was added, followed by further stirring for 2 hours. The solvent was then evaporated off under reduced pressure and the residue was extracted with ether. The extract was washed with water and concentrated to dryness. The residue was dissolved in 15 ml of toluene containing 3 g of dimethylamine, and the solution was allowed to stand for 3 days and concentrated. The residue was purified by silica gel column chromatography [eluent: methanol (first run), chloroform-methanol-water (65:25:4) (second run)]. The fractions containing the desired product were combined and concentrated to give 0.54 g of the above-identified compound as light-yellow syrup.

IR spectrum (film) cm$^{-1}$: 3400, 2970, 2930, 2860, 1665, 1450, 1385, 1230, 1085, 945, 820.

NMR spectrum (90 MHz, CDCl$_3$) δ: 1.59(9H, s), 1.65(6H, s), 2.00, 2.03(12H, m), 2.87(6H, s), 3.26(2H, br.), 3.43(3H, s), 3.50(3H, m), 3.99(2H, d), 4.25(2H, br.), 5.10(3H, m), 5.31(1H, t).

Elemental analysis: Calcd. for C$_{28}$H$_{52}$NO$_6$P.1.25-H$_2$O: C, 60.90; H, 9.94; N, 2.52; P, 5.61. Found: C, 60.73; H, 9.93; N, 2.52; P, 5.85.

EXAMPLE 5

3-Pentadecyloxy-2-methoxypropyl 2-dimethylaminoethyl phosphate (i) 3-Pentadecyloxy-2-methoxypropan-1-ol In a mixture of 30 ml of dimethyl sulfoxide (DMSO) and 30 ml of tetrahydrofuran (THF) were dissolved 10.9 g of 2-methylglycerol and 10 g of 1-bromopentadecane, and 7.7 g of powdered KOH was added at room temperature. The mixture was stirred vigorously for 30 minutes, refluxed for 3.5 hours, poured into 400 ml of water, neutralized with concentrated hydrochloric acid with ice-cooling, and extracted three times with ethyl acetate. The extract was washed with water, dried and concentrated to dryness. The oily residue (10 g) was purified by silica gel column chromatography [silica gel: 110 g; eluent: n-hexane-chloroform (2:3)] to give 4.6 g of the above-identified alcohol compound.

IR (liq) cm$^{-1}$: 3430, 2920, 2850, 1460, 1110, 750.

TLC: Rf=0.12 (silica gel, developing solvent: chloroform).

(ii) 3-Pentadecyloxy-2-methoxypropyl 2-dimethylaminoethyl phosphate

In 20 ml of benzene were dissolved 2.3 g (7.28 mmoles) of 3-pentadecyloxy-2-methoxypropanol and 2.8 g of 2-bromoethyl phosphorodichloridate, and 0.9 g of pyridine was added dropwise to the solution with stirring at room temperature. The mixture was further stirred at room temperature for 3 hours and concentrated to dryness. To the residue was added 20 ml of water and the mixture was refluxed for 1.5 hours and then cooled, followed by addition of 3 ml of concentrated hydrochloric acid. The mixture was extracted with ether and the extract was washed with water and concentrated to dryness. The residue was dissolved in 23 ml of 20% dimethylamine-toluene solution and the solution was allowed to stand at room temperature overnight and concentrated to dryness under reduced pressure. The residue was purified by silica gel (23 g) column chromatography, using methanol as an eluent to give the above-identified compound as a colorless powder. Yield 2.5 g (70.7%).

IR spectrum (KBr) cm$^{-1}$: 3420, 2920, 2850, 1465, 1230, 1090, 1065, 950, 800.

NMR spectrum (60 MHz, CDCl$_3$) δ: 0.88(3H), 1.25(26H), 2.83(6H), 3.1–3.87(10H), 3.87–4.5(4H), 7.75(1H).

Elemental analysis: Calcd. for $C_{23}H_{50}NO_6P \cdot H_2O$: C, 56.88; H, 10.79; N, 2.88; P, 6.38. Found: C, 56.85; H, 10.89; N, 2.65; P, 6.02.

EXAMPLE 6

3-Heptadecyloxy-2-methoxypropyl 2-dimethylaminoethyl phosphate (i) 3-Heptadecyloxy-2-methoxypropan-1ol 2-Methylglycerol (10.6 g) and 10.7 g of 1-bromoheptadecane were reacted and worked up in accordance with Example 5-(i) to give 5.2 g of the above-identified alcohol compound.

IR spectrum (film) cm$^{-1}$: 3450, 2920, 2850, 1460, 1370, 1115, 1050.

NMR spectrum (60 MHz, CDCl$_3$) δ: 0.88(3H), 1.29(30H), 2.13(1H), 3.20–3.90(10H).

(ii) 3-Heptadecyloxy-2-methoxypropyl 2-dimethylamino-ethyl phosphate

In 20 ml of benzene were dissolved 3.4 g of 3-heptadecyloxy-2-methoxypropanol and 4.11 g of 2-bromoethyl phosphorodichloridate, and 1.34 g of pyridine was added dropwise to the solution. The mixture was stirred at room temperature for 4 hours and concentrated to dryness under reduced pressure. The residue was dissolved in 34 ml of 20% dimethylamine-toluene. The solution was allowed to stand at room temperature overnight and then concentrated to dryness under reduced pressure. The residue was purified by silica gel (34 g) column chromatography using methanol as an eluent to give 3.2 g (62.3%) of the above-identified compound as a colorless powder.

IR spectrum (KBr) cm$^{-1}$: 3420, 2920, 2850, 1465, 1230, 1090, 1065, 950, 800.

NMR spectrum (60 MHz, CDCl$_3$) δ: 0.88(3H), 1.29(30H), 2.83(6H), 3.1—3.9(10H), 3.9–4.5(4H), 7.70(1H).

Elemental analysis: Calcd. for $C_{25}H_{54}NO_6P \cdot H_2O$: C, 58.45; H, 10.99; N, 2.73; P, 6.03. Found: C, 58.65; H, 11.02; N, 2.70; P, 6.23.

There can be obtained the following compounds in the same manner as the above Examples 1–6.

3-Pentadecyloxy-2-methoxypropyl 2-methylaminoethyl phosphate 3-(3,7,11,-Trimethyldodecyloxy)-2-methoxypropyl 2-dimethylaminoethyl phosphate 3-(3,7,11-Trimethyldodecyloxy)-2-methoxypropyl 2-methylaminoethyl phosphate 3-(3,7,11-Trimethyl-2,6,10-dodecatrienyloxy)-2-methoxypropyl 2-dimethylaminoethyl phosphate 3-(3,7,11-Trimethyl-2,6,10-dodecatrienyloxy)-2-methoxypropyl 2-methylaminoethyl phosphate 3-Hexadecyloxy-2-methoxypropyl 2-dimethylaminoethyl phosphate 3-Hexadecyloxy-2-methoxypropyl 2-methylaminoethyl phosphate 3-Heptadecyloxy-2-methoxypropyl 2-methylaminoethyl phosphate 3-(3-Heptadecenyloxy)-2-methoxypropyl 2-dimethylaminoethyl phosphate 3-(3Heptadecenyloxy)-2-methoxypropyl 2-methylaminoethyl phosphate 3-(9-Octadecenyloxy)-2-methoxypropyl 2-dimethylaminoethyl phosphate 3-(9-Octadecenyloxy)-2-methoxypropyl 2-methylaminoethyl phosphate 3-(9,12-Octadecadienyloxy)-2-methoxypropyl 2-dimethylaminoethyl phosphate 3-(9,12-Octadecadienyloxy)-2-methoxypropyl 2-methylaminoethyl phosphate 3-(9,12-Octadecadiynyloxy)-2-methoxypropyl 2-dimethylaminoethyl phosphate 3-(9,12-Octadecadiynyloxy)-2-methoxypropyl 2-methylaminoethyl phosphate 3-(9-Octadecanynyloxy)-2-methoxypropyl 2-dimethylaminoethyl phosphate 3-(9-Octadecanynyloxy)-2-methoxypropyl 2-methylaminoethyl phosphate 3-(6,10,14-Trimethylpentadecyloxy)-2-methoxypropyl 2-dimethylaminoethyl phosphate 3-(6,10,14-Trimethylpentadecyloxy)-2-methoxypropyl 2-methylaminoethyl phosphate 3-Nonadecyloxy-2-methoxypropyl 2-dimethylaminoethyl phosphate 3-Nonadecyloxy-2-methoxypropyl 2-methylaminoethyl phosphate 3-(7,11,15-Trimethylhexadecyloxy)-2-methoxypropyl 2-dimethylaminoethyl phosphate 3-(7,11,15-Trimethylhexadecyloxy)-2-methoxypropyl 2-methylaminoethyl phosphate 3-(9-Nonadecenyloxy)-2-methoxypropyl 2-dimethylaminoethyl phosphate 3-(9-Nonadecenyloxy)-2-methoxypropyl 2-methylaminoethyl phosphate 3-(7,11,15-Trimethyl-5-hexadecenyloxy)-2-methoxypropyl 2-dimethylaminoethyl phosphate 3-(7,11,15-Trimethyl-5-hexadecenyloxy)-2-methoxypropyl 2-methylaminoethyl phosphate 3-Eicosanyloxy-2-methoxypropyl 2-dimethylaminoethyl phosphate 3-Eicosanyloxy-2-methoxypropyl 2-methylaminoethyl phosphate 3-(3,7,11,15-Tetramethylhexadecyloxy)-2-methoxypropyl 2-dimethylaminoethyl phosphate 3-(3,7,11,15-Tetramethylhexadecyloxy)-2-methoxypropyl 2-methylaminoethyl phosphate 3-(6,10,14-Trimethylheptadecyloxy)-2-methoxypropyl 2-dimethylaminoethyl phosphate 3-(6,10,14-Trimethylheptadecyloxy)-2-methoxypropyl 2-methylaminoethyl phosphate 3-(3,7,11,15-Tetramethyl-2,6,10,14-Hexadecatetraenyloxy)-2-methoxypropyl 2-methylaminoethyl phosphate

PREPARATION EXAMPLE 1

In 1.0 liter of distilled water is dissolved 80 g of 3-octadecyloxy-2-methoxypropyl 2-dimethylaminoethyl phosphate, and after bacterial filtration, the solution is aseptically distributed in 1 ml portions into 1000 vials and lyophilized. After drying, the vials are sealed.

On the other hand, 2 liters of distilled water for injection containing 100 g of xylitol or mannitol is aseptically distributed in 2 ml portions into 1000 injection ampules which are then fushion-sealed.

For administration, one vial equivalent of this powder is extemporaneously dissolved in xylitol (or mannitol) solution for injection.

PREPARATION EXAMPLE 2

Tablets

Per tablet,
(1) 100 mg of 3-octadecyloxy-2:methoxypropyl 2-dimethylaminoethyl phosphate,
(2) 200 mg of lactose,
(3) 51 mg of corn starch, and
(4) 9 mg of hydroxypropylcellulose
are mixed and granulated in the conventional manner. Then, corn starch (8 mg) and magnesium stearate (2 mg) are added and the mixture is tableted to give a 370 mg of tablet, 9.5 mm in diameter.

PREPARATION EXAMPLE 3

The tablet prepared in 2 above, is coated with an acetone-ethanol (4:6) solution containing hydroxypropylmehtylcellulose phthalate (14 mg) and castor oil (1 mg) in a concentration of 7% to give an enteric-coated tablet.

TEST EXAMPLE 1

Antitumor activity of 3-octadecyloxy-2-methoxypropyl 2-dimethylaminoethyl phosphate (Example 1)

One mg/mouse of the compound of Example 1 was dissolved in physiological saline and intraperitoneally administered to ICR mice (5 individuals per group). On the 4th day, $1 \times 10^5$ Sarcoma 180 cells per mouse were intraperitoneally transplanted. In the drug administration group, 2 of the 5 mice were still alive on the 60th day and the life span prolonging rate relative to the control group (T/C) was 250.

When the control drug (IX) was administered under the same conditions, none of the mice was alive on the 60th day and the T/C rate was 170.

TEST EXAMPLE 2

Antitumor activity of (2S)-3-octadecyloxy-2-methoxypropyl 2-dimethylaminoethyl phosphate (Example 2)

To ICR mice (5 individuals per group), $1 \times 10^5$ Sarcoma 180 cells/mouse were intraperitoneally transplanted. Then, 1 mg/mouse of the compound of Example 2 was dissolved in physiological saline and administered. In the drug administration group, one mouse was alive on the 60th day and the life span prolonging rate relative to the drug-free control group was 240.

TEST EXAMPLE 3

Antitumor activity of 3-octadecyloxy-2-methoxypropyl 2-methylaminoethyl phosphate (Example 3)

The procedure of Test Example 2 was repeated except that the compound of Example 3 was used in lieu of the compound of Example 2. Of the 5 mice, 2 were alive on the 60th day and the life span prolonging rate was 396.

TEST EXAMPLE 4

Antitumor activity against MM46 mammary cancer cells

To C3H/He mice (5 individuals per group), $1 \times 10^5$ MM46 mammary cells/mouse were intraperitoneally transplanted and 250 μg/mouse/day of the drug was administered once daily for a total of 8 times, i.e. during 4 days from day 5 to day 2 before the transplantation and, again, 4 days from day 2 to day 5 after the transplantation or a total of 8 days. Table 1 shows the results in comparison with the results for the drug-free control group.

TABLE 1

Antitumor activity in MM 46 tumor-bearing mice

| Test compound (Example No.) | Survival time prolongation rate (T/C) | Number of surviving mice*/ number of mice used |
|---|---|---|
| 1 | 330 | 4/5 |
| 2 | 315 | 4/5 |
| Positive control compound (IX) | 246 | 2/5 |

*Number of surviving mice on the 60th day.

TEST EXAMPLE 5

Action on blood platelets

Method and results

From male rabbits, the blood was collected using an injection syringe containing 3.15% citric acid as an anticoagulant (in a ratio of 1 part per 9 parts of blood) and centrifuged at 1000 rpm for 10 minutes at room temperature to give a platelet-rich plasma (PRP). This PRP was further centrifuged at 1400 rpm for 15 minutes to give a platelet pellet. The pellet was suspended in $Ca^{++}$-free Tyrode solution (containing 0.25% of gelatin) to give a washed PRP. This washed PRP (250 μl) was stirred at 37° C. for 2 minutes and, then, 25 μl of 0.2 to 0.5 mM $Ca^{++}$ was added. The mixture was further stirred for 30 seconds, at the end of which time the test drug was added thereto at the level of $3 \times 10^{-5}$ M. The degree of platelet aggregation was determined with an aggregometer (Rika Denki K.K.). Whereas the control compound (IX) showed an aggregation of 46 to 63%, none of the compounds of Example 1 to 4 caused the aggregation.

TEST EXAMPLE 6

Blood pressure depression effect

Male Sprague-Dawley rats, 7 weeks old and weighing 200 to 290 g, were anesthetized with pentobarbital sodium (60 mg/kg, intraperitoneal) and cannulas were inserted into the left carotid artery (for blood pressure measurement) and the left femoral vein (for intravenous drug administration). Whereas 300 μg/kg of control compound (IX) caused a blood pressure depression of 43 to 75 mmHg, none of the compounds of Examples 1 to 4 showed blood pressure depression activity.

What is claimed is:
1. A compound of the formula

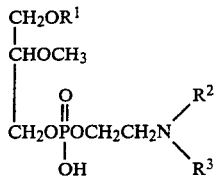

wherein $R^1$ is an alkyl, alkenyl or alkynyl group of 15 to 20 carbon atoms, $R^2$ is an alkyl group of 1 to 4 carbon atoms and $R^3$ is a hydrogen atom or an alkyl group of 1 to 4 carbon atoms, or a pharmaceutically acceptable salt thereof.

2. A compound according to claim 1, wherein $R^1$ is an alkyl, alkenyl or alkynyl group of 15 to 17 carbon atoms.

3. A compound according to claim 1, wherein $R^1$ is an alkyl, alkenyl or alkynyl group of 18 carbon atoms.

4. A compound according to claim 1, wherein $R^1$ is an alkyl, alkenyl or alkynyl group of 19 or 20 carbon atoms.

5. A compound according to claim 1, wherein $R^1$ is n-octadecyl.

6. A compound according to claim 1, wherein $R^2$ is methyl.

7. A compound according to claim 1, wherein $R^3$ is hydrogen or methyl.

8. The compound which is 3-octadecyloxy-2-methoxypropyl 2-dimethylaminoethyl phosphate.

9. The compound which is 3-octadecyloxy-2-methoxypropyl 2-methylaminoethyl phosphate.

10. The compound of claim 1 which is (2S)-3-octadecyloxy-2-methoxypropyl 2-dimethylaminoethyl phosphate.

* * * * *